United States Patent [19]

Mikitenko et al.

[11] 4,302,298

[45] Nov. 24, 1981

[54] PROCESS FOR ISOLATING METHYL TERT-BUTYL ETHER FROM THE REACTION PRODUCTS OF METHANOL WITH A $C_4$ HYDROCARBON CUT CONTAINING ISOBUTENE

[75] Inventors: Paul Mikitenko, Noisy le Roi; Lionel Asselineau, Paris, both of France

[73] Assignee: Institut Francais du Petrole, Rueil-Malmaison, France

[21] Appl. No.: 123,539

[22] Filed: Feb. 22, 1980

[30] Foreign Application Priority Data

Feb. 22, 1979 [FR] France ............................... 79 04786

[51] Int. Cl.³ .............................................. B01D 3/14
[52] U.S. Cl. ......................................... 203/75; 203/76; 203/77; 203/78; 203/79; 203/80; 203/82; 203/83; 203/84; 203/85; 203/93; 203/94; 568/697; 568/699
[58] Field of Search ............................. 568/697, 699; 203/DIG. 23, 39, 40, 42, 95–97, 12, 14, 76, 77–80, 82–85, 91, 93, 94

[56] References Cited

U.S. PATENT DOCUMENTS

| | | | |
|---|---|---|---|
| 3,940,450 | 2/1976 | Lee | 568/699 |
| 4,118,425 | 10/1978 | Herbstman | 568/697 |
| 4,198,530 | 4/1980 | Wentzheimer et al. | 568/699 |

*Primary Examiner*—Frank Sever
*Attorney, Agent, or Firm*—Millen & White

[57] ABSTRACT

Process for isolating methyl tert-butyl ether contained in the reaction product of methanol with a $C_4$ hydrocarbon cut containing isobutene, comprising fractionating said reaction product by introducing it at an intermediate point of a distillation zone, recovering methyl tert-butyl ether at the bottom thereof and, at the top thereof, a mixture of $C_4$ hydrocarbons with methanol which is washed with water and condensed and wherefrom is separated a condensed $C_4$ hydrocarbon fraction, a portion of which is fed back as reflux to the top of the distillation zone and another portion discharged, and separating the remaining water-methanol mixture by distillation.

15 Claims, 1 Drawing Figure

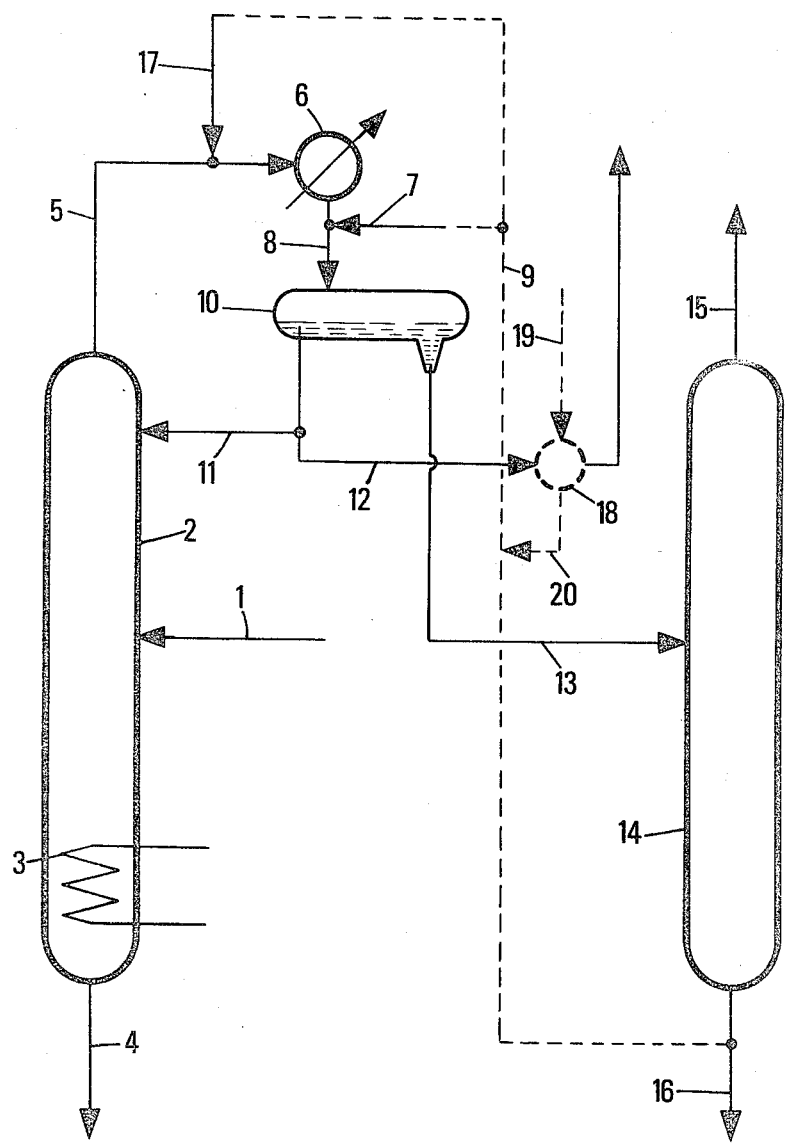

PROCESS FOR ISOLATING METHYL TERT-BUTYL ETHER FROM THE REACTION PRODUCTS OF METHANOL WITH A C4 HYDROCARBON CUT CONTAINING ISOBUTENE

BACKGROUND OF THE INVENTION

This invention relates to the production of methyl tert-butyl ether (MTBE); it concerns more particularly the isolation of said compound from the reaction product of methanol with a hydrocarbon cut containing isobutene.

Methyltert-butyl ether is known as a valuable industrial product; in particular its incorporation to fuels for controlled ignition engines provides gasolines of high octane number, particularly lead-free gasolines or gasolines of reduced lead content.

A difficulty in its preparation is due to the fact that the reaction of isobutene with methanol is a balanced reaction; it is consequently advantageous to proceed in the presence of an excess of one of the reactants, for example of methanol. However, when making use of a methanol excess or of an equimolecular mixture of the reactants, there is obtained, in practically all cases, a mixture containing methyl tert-butyl ether, methanol and hydrocarbons, for example the $C_4$ hydrocarbons which were associated with the isobutene in the feed charge to the process as well as unconverted isobutene. The fractionation of these compounds by distillation is difficult to perform in view of the formation of azeotropes: the azeotrope of methanol with methyl tert-butyl ether and azeotropes of the $C_4$ hydrocarbons with methanol.

Many proposals have been made for performing these fractionations but none of them is entirely satisfactory. Washing with water, for example, makes it possible to remove a substantial fraction of the methanol, but results in the presence of traces of water in the MTBE, which is a disadvantage for the incorporation of said ether to motor gasolines.

The distillation of the methanol / MTBE azeotrope is not advantageous in view, on the one hand, of the low methanol content of said azeotrope, even when operating under high pressures and, on the other hand, of the necessity to recycle said azeotrope to the reactor, which is unfavorable to the progress of the reaction.

The distillation of the methanol/MTBE/$C_4$ hydrocarbons mixture, as issued from the zone of reaction of methanol with the $C_4$ cut, is itself of low efficiency in view of the low methanol content of the methanol-$C_4$ hydrocarbon azeotropes, even when proceeding under high pressure and at a high reflux rate.

SUMMARY OF THE INVENTION

Detailed Description

It has been found, and this is the object of the invention, that the distillation of the MTBE-methanol-$C_4$ hydrocarbons mixture is much more efficient when it is performed with the use, as reflux, of the condensed top vapors, freed from the methanol contained therein by means of a convenient technique, for example by washing with water. This fact is illustrated, for example, by the following table which summarizes the results of two distillations of a charge containing MTBE (53%), methanol (7.8%) and $C_4$ hydrocarbons (39.2%), in a 40 plate column, under a pressure of 16 atmospheres, with the same reflux rate of 1.1, one of the distillations being performed with ordinary reflux and the other with a reflux freed of methanol by washing with water. In both cases, the $C_4$ hydrocarbons are recovered substantially completely at the top of the column.

| | DISTILLATION WITH ORDINARY REFLUX | DISTILLATION WITH WASHED REFLUX |
| --- | --- | --- |
| Methanol removal rate at the top % | 71.8 | 80.6 |
| MTBE recovery rate at the bottom % | 90.7 | 94.3 |
| Heat supplied to the boiler (Kcal/kg of charge) | 101 | 94 |

Depending on the charge to be distilled and the desired specification for the products, it also appeared as optionally advantageous, from the point of view of the heat consumed for the distillation, to introduce the washed reflux at two separate levels of the upper part of the column.

The process of the invention consists consequently of: (a) introducing the mixture to be fractionated, which comprises MTBE, methanol and $C_4$ hydrocarbons and includes residual isobutene, into a distillation zone, at an intermediate point thereof, (b) recovering MTBE from the bottom of said zone and recovering, at the top thereof, a mixture essentially consisting of $C_4$ hydrocarbons and methanol, (c) washing said mixture with water in a washing zone, (d) separating a condensed $C_4$ hydrocarbon fraction from a condensed water-methanol fraction, (e) feeding back a portion of the condensed and separated $C_4$ hydrocarbon fraction to the distillation zone, at least 25% of said portion being fed back to the top of said zone, (f) discharging the other portion of the separated and condensed hydrocarbon fraction and (g) distilling the water/methanol fraction so as to separately recover water and methanol.

The so-recovered water may be fed back, at least partly, to the washing zone and methanol may be recycled, at least partly, to the reactor for the production of MTBE. The discharged hydrocarbon fraction does not normally contain isobutene in a sufficient amount to justify its recycling; it can therefore be used for other purposes, optionally after a complementary washing with water, preferably with the water recovered from step (g).

It is accordingly an essential feature of the process to feed back, as reflux, to the distillation zone, at least one portion of the condensed hydrocarbon fraction separated from the water/methanol phase. This fraction may be fed back as such, without drying, which constitutes a substantial advantage of the process.

The point of introduction of said fraction into the column has a certain importance. It is preferred to feed the totality of said fraction to the top of the column, although it is also possible, in some cases, to introduce a portion of said fraction at the top and another portion at at least one lower point of the column, which must not be lower, however, than the point of introduction of the charge.

The reflux ratio is also important. It ranges advantageously from 0.3 to 10, preferably from 0.5 to 5, said ratio being defined as the ratio of the amount of hydrocarbon phase fed back to the column (step e) to the amount of hydrocarbon phase discharged from the plant (step f), these amounts being expressed by weight.

The washing with water of the top effluent of the column constitutes another important feature of the process. This washing may be performed on the vapor effluent from the distillation zone, before cooling and condensation thereof; it may also be performed after condensation of said effluent. The washing may be conducted in any known manner, for example by admixture in line, in a countercurrent contact zone, in a watering tower, etc.

In view of the high solubility of methanol in water, the amount of water is not necessarily very substantial, it depends on the efficiency of the selected washing technique and on the desired result. For economic reasons, it is preferred to proceed with a wash which removes at least 50%, and more advantageously at least 90% of the methanol present in the top effluent of the distillation zone. It is also possible, if so desired, to proceed with a further wash with water of the hydrocarbon fraction discharged from the process, after it has been separated from the fraction fed back as reflux.

The distillation is conducted under a superatmospheric pressure of, for example, 2 to 30 absolute bars, and preferably 4 to 20 absolute bars, so as to take advantage of a more favorable composition of the methanol/$C_4$ hydrocarbon azeotrope.

The temperatures at the top and at the bottom of the column depend on the selected pressure. Within the above-mentioned preferred pressure range, the top temperature may be from 35° to 105° C. and the bottom temperature from 100° to 190° C.

MTBE may be withdrawn in the liquid state from the bottom of the column or in the vapor state from the lower portion of the column, but above the liquid phase of the column bottom or above the reboiler.

The reaction of methanol with the isobutene of a $C_4$ cut is well known and needs not to be further described here. It is frequently conducted at 20°–130° C., in the presence of an acid catalyst such as a sulfonic ion-exchange resin in the acid form.

The $C_4$ cut, whose isobutene content is comprised, for example, between 20 and 70% by weight, may be any of cuts already proposed for this type of reaction. It may be issued, for example, from a hydrocarbon cracking, steam-cracking or dehydrogenation unit.

BRIEF DESCRIPTION OF THE DRAWING

The invention is illustrated by the accompanying drawing, by way of example, which is a schematic flowchart of the process.

DETAILED DESCRIPTION OF THE DRAWING

The mixture to be separated (MTBE, methanol, $C_4$ hydrocarbons) is introduced through line 1 into column 2 and heated by the heat exchanger 3. MTBE is withdrawn from the bottom through line 4. At the top, a vapor is withdrawn through line 5; this vapor is condensed in condenser 6, cooled down with water or otherwise. The condensate is washed in line 8 with water introduced through line 7 or 17. The latter may be fresh water or water recycled through the dotted line 9.

The washed condensate is separated into two phases in decanter 10: the upper hydrocarbon phase is withdrawn and divided into a reflux fraction (line 11) and a fraction (line 12) which is discharged from the unit, optionally after washing with additional water in washer 18, fed with water (preferably issued from line 16) through line 19, which may then be fed back to line 9 through duct 20. The water/methanol phase is fed through line 13 to the distillation column 14 operated under known conditions and, for example, at atmospheric pressure. At the top, through line 15, there is recovered methanol which can be fed to the MTBE production reactor. The water is discharged from the column bottom through line 16.

EXAMPLE 1

An effluent from a MTBE production reactor having the following composition by weight:

| | |
|---|---|
| Isobutane: | 2.20 |
| Isobutene: | 1.84 |
| 1-Butene: | 19.41 |
| Butane: | 6.50 |
| 2 t-Butene: | 7.88 |
| 2 c-Butene: | 3.55 |
| MTBE: | 53.2 |
| Methanol: | 4.92 |
| Miscellaneous: | 0.5 | is fed, at a rate of 5000 g/h, onto the $20^{th}$ plate (from the bottom) of a column (2) of 50 bubble-trays, having a diameter of 110 mm, operated under a pressure of 4.7 atmospheres. The amount of heat supplied to the boiler of the column is so adjusted as to obtain, at the top, substantially all the paraffinic and olefinic $C_4$ hydrocarbons. Under these conditions, there is established a temperature profile in the column whose limit values are 45° C. at the top and 105° C. at the bottom.

On the line containing the top vapors, before the condenser, there is injected water in the liquid state at a rate of 925 g/h.

After the condenser, the condensed top vapors and the introduced water are separated in two liquid phases in a reflux drum specially arranged for a convenient decantation.

A portion of the upper liquid phase, amounting to 6400 g/h, is recycled to the top of the column, as reflux; a second portion of said phase, amounting to 5800 g/h, is recycled to the column, onto the $30^{th}$ plate. A third portion, amounting to 2053 g/h, which constitutes the distillate, is discharged from the unit. The analysis of the distillate shows that it contains 99.8% of $C_4$ hydrocarbons, the only impurities, which are present as traces, being methanol and MTBE.

The lower liquid phase consists of an aqueous solution of methanol. It contains more than 90% of the methanol discharged from the top of the column. This liquid phase is fed to a supplemental column (14), of 40 plates, used for regenerating methanol and recycling it to the MTBE production reactor.

The product from the bottom of column (2) is discharged from the unit at an average rate of 2704 g/h. It consists of 98.3% MTBE, 0.58% $C_4$ hydrocarbons, 0.2% methanol and 0.92% various products heavier than methanol.

EXAMPLE 2

The distillation described in example 1 is repeated under the same conditions with respect to the composition and flow rate of the charge and the geometry of the column, but under an operating pressure of 10 atmospheres. The operating conditions of column (2) are again so adjusted as to obtain at the top substantially all the $C_4$ hydrocarbons. The temperature profile which is then established ranges from 75° C. at the top to 150° C.

at the bottom of the column. After injection of 1000 g/h of water, obtained from the fine washing of the distillate, on the line containing the top vapors, condensation of these vapors and decantation at 65° C., a portion of the upper phase (freed from more than 90% of its methanol content), amounting to 2050 g, is fed back as reflux to the column, a second portion, amounting to 2480 g, is fed back to the column on the 30$^{th}$ plate, while a third portion constituting the distillate, amounting to 2053 g as an average, is fed to a mixer-decanter apparatus where it is subjected to a fine washing with 1000 g/h of water. At the outlet from this washing unit, the distillate consists of substantially pure $C_4$ hydrocarbons, whose methanol content is lower than 50 ppm.

At the bottom of the column (2), pure MTBE is withdrawn, whose characteristics are similar to those reported in example 1.

What is claimed is:

1. In a process for isolating methyl tert-butyl ether (MTBE) from the products of reaction of methanol with a $C_4$ hydrocarbon cut containing isobutene, comprising the steps of (a) introducing a feed mixture of said reaction products, comprising MTBE, methanol and $C_4$ hydrocarbons including residual isobutene, into a superatmospheric distillation zone, at an intermediate point thereof, (b) recovering MTBE from the bottom of said zone and a mixture of $C_4$ hydrocarbons with methanol from the top thereof, (c) washing said mixture recovered from step (b) with water in a washing zone, and (d) separating and recovering a washed condensed $C_4$ hydrocarbon fraction and a condensed water/methanol fraction, the improvement comprising recycling a portion of the washed, condensed and separated substantially water free $C_4$ hydrocarbon fraction to the distillation zone as reflux, at least 25% of said portion being recycled to the top of said zone; thereby increasing the rate of recovery of MTBE, decreasing the methanol content thereof and decreasing the heat consumption of the distillation zone.

2. A process according to claim 1 wherein all of said washed, condensed and separated $C_4$ hydrocarbon portion recycled to the distillation zone is fed to the top of said zone.

3. A process according to claim 1, operated at a reflux ratio of from 0.3 to 10, said ratio being the ratio of the portion of said separated $C_4$ hydrocarbon fraction recycled to the distillation zone to the non-recycled $C_4$ hydrocarbon portion.

4. A process according to claim 3, wherein the pressure in the distillation zone of step (a) is from 2 to 30 bars, the temperature at the top being from 35°–105° C. and the temperature at the bottom being 100°–190° C.

5. A process according to claim 4 wherein the pressure is from 4 to 20 bars.

6. A process according to claim 3, operated at a reflux ratio of 0.5 to 5.

7. A process according to claim 6, wherein, in step (c), the washing is performed so as to recover in the aqueous phase at least 90% of the methanol contained in the mixture of the $C_4$ hydrocarbons with methanol.

8. A process according to claim 3, wherein in step (c) the washing is performed so as to recover in the aqueous phase at least 50% of the methanol contained in the mixture of the $C_4$ hydrocarbons with methanol.

9. A process according to claim 1, wherein the portion of the $C_4$ hydrocarbon fraction recycled to the distillation zone which is not fed to the top of said zone, is fed at one or more points below said top but not lower than said intermediate point.

10. A process according to claim 1, wherein in step (c) the washing is performed so as to recover in the aqueous phase at least 50% of the methanol contained in the mixture of the $C_4$ hydrocarbons with methanol recovered from step (b).

11. A process according to of claim 1, wherein, in step (c), the washing is performed so as to recover in the aqueous phase at least 90% of the methanol contained in the mixture of the $C_4$ hydrocarbons with methanol recovered from step (b).

12. A process according to claim 1, comprising the further steps of (f) discharging the other portion of the condensed and separated hydrocarbon fraction and (g) distilling the water/methanol fraction for recovering separately water and methanol.

13. A process according to claim 12, wherein the methanol recovered in step (g) is recycled to the unit for producing MTBE by reacting methanol with a $C_4$ hydrocarbon cut containing isobutene.

14. A process according to of claim 12, wherein the hydrocarbon fraction discharged in step (f) is subjected to an additional washing by means of at least one portion of the water recovered from step (g).

15. A process according to claim 1, wherein the washing step (c) comprises injecting water into overhead vapors from the column and then condensing the resultant mixture.

* * * * *